United States Patent
Sporbert et al.

(10) Patent No.: US 8,142,187 B2
(45) Date of Patent: Mar. 27, 2012

(54) METHOD AND APPARATUS FOR DIGITALLY EVALUATING INSERTION QUALITY OF CUSTOMIZED ORTHODONTIC ARCH WIRE

(75) Inventors: Peer Sporbert, Berlin (DE); Dimitij Kouzian, Berlin (DE); Hans Imgrund, Berlin (DE); Stephan Maetzel, Berlin (DE)

(73) Assignee: Orametrix, Inc., Richardson, TX (US)

( * ) Notice: Subject to any disclaimer, the term of this patent is extended or adjusted under 35 U.S.C. 154(b) by 186 days.

(21) Appl. No.: 12/606,033

(22) Filed: Oct. 26, 2009

(65) Prior Publication Data

US 2010/0106465 A1 Apr. 29, 2010

Related U.S. Application Data

(62) Division of application No. 11/233,946, filed on Sep. 23, 2005, now Pat. No. 7,641,473.

(51) Int. Cl.
*A61C 3/00* (2006.01)
(52) U.S. Cl. .......................................... 433/24
(58) Field of Classification Search .................... 433/24, 433/215, 8, 20, 22
See application file for complete search history.

(56) References Cited

U.S. PATENT DOCUMENTS

| | | | |
|---|---|---|---|
| 6,648,640 B2 * | 11/2003 | Rubbert et al. | 433/24 |
| 2002/0150859 A1 * | 10/2002 | Imgrund et al. | 433/24 |
| 2003/0096210 A1 * | 5/2003 | Rubbert et al. | 433/24 |
| 2004/0115586 A1 * | 6/2004 | Andreiko et al. | 433/3 |

* cited by examiner

*Primary Examiner* — Sunil K Singh
(74) *Attorney, Agent, or Firm* — Jasvantrai C. Shah

(57) ABSTRACT

A method and apparatus is provided for digitally checking the insertion quality of a target customized virtual arch wire designed during treatment planning prior to actually manufacturing the target arch wire. The method includes the steps of digitally simulating the insertion of the customized target virtual arch wire into the virtual brackets placed up on virtual teeth of a patient in an initial state of interest for checking if the arch wire could be inserted into the virtual brackets without conflicts or collisions. The initial state may be a malocclusion state or any intermediate treatment state of the patient. In the event the target virtual arch wire would cause conflicts, then the simulation optimizes the arch wire design in an attempt to eliminate the conflicts. In another aspect, a method is provided for selecting the recommended starting point for inserting the customized arch wire in the brackets placed on the dentition of the patient in the initial state.

7 Claims, 13 Drawing Sheets

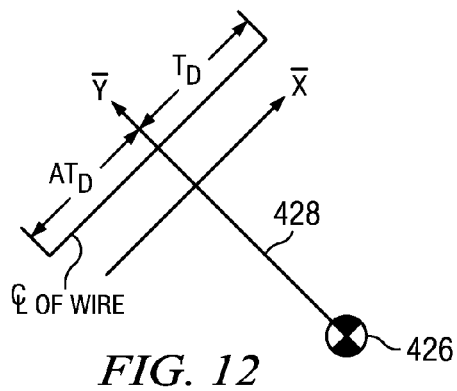
FIG. 12
$$\begin{bmatrix} 0.4 & -0.7 & 0 & -22 \\ 0.9 & 0.7 & 0 & 21 \\ 0 & 0.14 & 0 & 2 \\ 0 & 0 & 0 & 1 \end{bmatrix}$$
FIG. 13
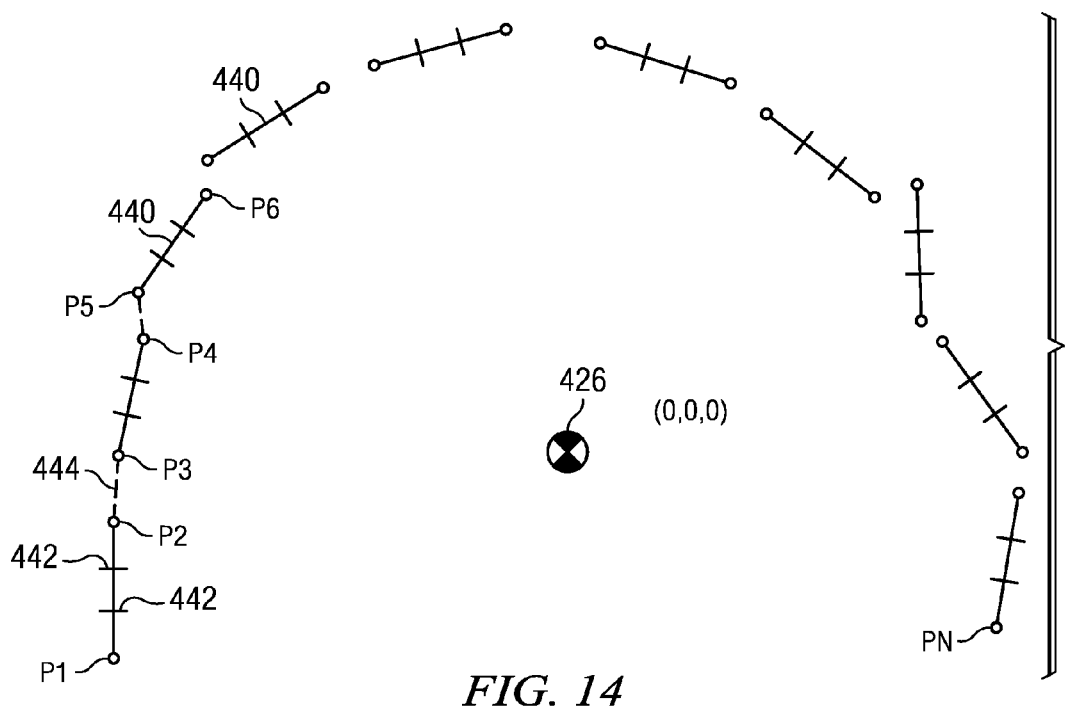
FIG. 14

METHOD AND APPARATUS FOR DIGITALLY EVALUATING INSERTION QUALITY OF CUSTOMIZED ORTHODONTIC ARCH WIRE

CROSS-REFERENCE TO RELATED APPLICATIONS

This application is a divisional application of the U.S. patent application Ser. No. 11/233,946, filed Sep. 23, 2005, now issued as U.S. Pat. No. 7,641,473; and related to another divisional application of the same parent application, U.S. patent application Ser. No. 12/606,071, filed concurrently with the instant application. The entire contents of each of the above-referenced patent applications are incorporated by reference herein.

BACKGROUND OF THE INVENTION

A. Field of the Invention

This invention relates to the field of computerized techniques for orthodontic treatment planning for human patients. More particularly, the invention is directed to a method and apparatus for checking if a target virtual orthodontic arch wire can be inserted into virtual brackets placed on the virtual malocclusion dentition of a patient without conflicts. Additionally, the invention discloses a process whereby the target orthodontic virtual arch wire can be redesigned in case of insertion conflicts.

B. Description of Related Art

In orthodontics, a patient suffering from a malocclusion is treated by affixing brackets to the surface of the teeth and installing an arch wire in the slots of the brackets. The arch wire and brackets are designed to generate a customized force system that applies forces to teeth, by which individual teeth are moved relative to surrounding anatomical structures into a desired occlusion. There are two basic approaches to designing an appropriate force system for a patient. One is based on a straight arch wire and customized brackets, e.g., Andreiko et al., U.S. Pat. No. 5,447,432. The other is based on off-the shelf brackets and designing a customized arch wire that has complex bends and twists designed to move or rotate the teeth in the desired direction. Traditionally, the latter approach has required manual bending of the arch wire by the orthodontist.

In recent years, computer-based approaches have been proposed for aiding orthodontists in their practice. However, these approaches are limited to diagnosis and treatment planning of craniofacial structures, including the straightening of teeth. For example, U.S. Pat. No. 6,648,640 to Rubbert, et al. describes an interactive, computer based orthodontist treatment planning, appliance design and appliance manufacturing. A scanner is described which acquires images of the dentition, which are converted to three-dimensional frames of data. The data from the several frames are registered to each other to provide a complete three-dimensional virtual model of the dentition. Individual tooth objects are obtained from the virtual model. A computer-interactive software program provides for treatment planning, diagnosis and appliance design from the virtual tooth models. A desired occlusion for the patient is obtained from the treatment planning software. The virtual model of the desired occlusion and the virtual model of the original dentition provide a base of information for custom manufacture of an orthodontic appliance. A variety of possible appliance and appliance manufacturing systems are contemplated, including customized arch wires and customized devices for placement of off-the shelf brackets on the patient's dentition for housing the arch wires, and removable orthodontic appliances.

U.S. Pat. No. 6,632,089 to Rubbert, et al. describes an interactive, software-based treatment planning method to correct a malocclusion. The method can be performed on an orthodontic workstation in a clinic or at a remote location such as a lab or precision appliance-manufacturing center. The workstation stores a virtual three-dimensional model of the dentition of a patient and patient records. The virtual model is manipulated by the user to define a target situation for the patient, including a target arch-form and individual tooth positions in the arch-form. Parameters for an orthodontic appliance, such as the location of orthodontic brackets and resulting shape of an orthodontic arch wire, are obtained from the simulation of tooth movement to the target situation and the placement position of virtual brackets. The treatment planning can also be executed remotely by a precision appliance service center having access to the virtual model of the dentition. In the latter situation, the proposed treatment plan is sent to the clinic for review, and modification or approval by the orthodontist. The method is suitable for other orthodontic appliance systems, including removable appliances such as transparent aligning trays.

Machines for bending orthodontic arch wires have been proposed in the prior art. Andreiko et al. describes an apparatus that takes a straight arch wire and imparts a simple planar arcuate curvature to the wire. The wire is customized in the sense that the shape of the arc is designed for a particular patient, but the wire bending apparatus described in Andreiko et al. is limited to a customized bracket approach to orthodontics. In particular, the Andreiko et al. wire bending apparatus cannot produce any complex bends and twists in the wire, e.g., bends requiring a combination of translation and rotational motion.

U.S. Pat. No. 6,612,143 to Butscher, et al. describes a robot and method for automatically bending orthodontic arch wires, retainers, or other orthodontic or medical devices into a particular shape. In particular, the disclosure enables the manufacture of custom, highly accurate orthodontic arch wires. Such wires are ideally suited to an arch wire-based orthodontic treatment regime based on standard, off-the-shelf brackets.

If a customized arch wire cannot be properly inserted into the brackets on the dentition of the patient in the malocclusion state, then its effectiveness may be diminished or lost; and in some instances, the arch wire may have to be discarded and a new one may have to be designed. This is likely to increase the treatment time and cost. The art is lacking in tools that would enable a practitioner in checking if a target virtual orthodontic arch wire can be inserted into virtual brackets placed on the virtual malocclusion dentition of a patient without conflicts in advance of actually placing the real arch wire in the real brackets placed on the dentition of the patient.

The present invention addresses this deficiency in the art and offers a method and apparatus for checking if a target virtual orthodontic arch wire can be inserted into virtual brackets placed on the virtual malocclusion dentition of a patient without conflicts prior to actually manufacturing the arch wire. Additionally, the invention discloses a process whereby the target virtual orthodontic arch wire can be redesigned in case of insertion conflicts.

SUMMARY OF THE INVENTION

In a first aspect of the invention, a method is provided for digitally checking the insertion quality of a customized target virtual arch wire designed during treatment planning prior to actually manufacturing the target arch wire. The method includes the steps of digitally simulating the insertion of the virtual arch wire into the virtual brackets placed up on virtual teeth of a patient in an initial state of interest for checking if the target virtual arch wire could be inserted into the virtual brackets without conflicts. The custom arch wire comprises alternating sequence of straight segments and bent segments, which typically give the wire a non-planar shape. For correct insertion of the arch wire, only the straight segments should go into the bracket slots. In the event that a portion of a bent segment winds up in a bracket slot during the arch wire insertion into the brackets, then that is identified as a conflict or a collision. Conflicts are undesirable since they cause the arch wire to loose its effectiveness in terms of moving the patient's teeth from, say malocclusion state to the target state. The straight segments are designed to be longer in length than the corresponding bracket slots so as to provide some sliding room for the arch wire as the teeth move from malocclusion to the target finish position.

The method includes the step of selecting a virtual bracket slot as a starting point. Then, the arch wire insertion between the selected bracket slot and its adjacent neighbour bracket slot is evaluated. Subsequently, the neighbour is designated as the selected bracket slot and the arch wire insertion is evaluated between it and its adjacent neighbour. In this manner, all neighbours on one side of the starting point bracket are successively evaluated first, and then on the other side, so as to evaluate the insertion quality of the entire arch wire.

In another aspect of the invention, a measured force is applied to the virtual arch wire in an incremental manner for inserting the arch wire into the selected bracket slot. The to incremental process of applying the force is stopped when the designated virtual arch wire straight segment is positioned in the corresponding virtual bracket slot within a given tolerance. That means the designated straight segment of the virtual arch wire is properly inserted into the virtual bracket slot without a conflict or a collision.

In another aspect of the invention, even after applying the sufficient force, if the arch wire insertion into the neighbor causes a conflict or a collision, then the conflict is recorded and the insertion process continued until the entire wire is checked out. In case of conflicts, first the arch wire insertion is again checked out with repositioning the straight segments of the virtual arch wire in the bracket slots. Then, if the repositioning removes all the conflicts, then the arch wire is deemed to have no conflicts. On the other hand, if the conflicts persist, then the optimization step is performed where by the length of the straight segment designated for the neighbor bracket slot is modified to see if the conflict or the collision can be removed. It may be recalled that a conflict or a collision is created when a portion of a bent segment gets unavoidably inserted into a bracket slot during the arch wire insertion process. If the conflict or the collision can be removed in this manner, i.e. by modifying the straight segment length, than that is recorded as a potential arch wire design modification. On the other hand, if the conflict persists in spite of the optimization, then the optimization step has failed, and the conflict is recorded at the neighbor. The length of a straight segment that is in excess of the corresponding bracket slot length is herein referred to as the 'designed sliding ways'. Throughout the wire insertion process, at the conclusion of the wire insertion step at a bracket, a running log of the actual sliding ways and the wire insertion depth within the bracket slot is maintained.

The method described above is summarized as follows:
The method of digitally evaluating the insertion quality of a target custom virtual arch to wire, comprising the steps of:

(a) obtaining a model of a set of virtual of brackets placed up on the virtual teeth of a patient in a jaw in an initial state;

(b) obtaining a virtual model of a target custom arch wire designed to be inserted into said virtual brackets; wherein the custom arch wire comprises alternating sequence of straight segments and bent segments; wherein each of the straight segments is designated to be inserted into the slot of a specific virtual bracket from the set of virtual brackets;

(c) selecting a first virtual bracket from the set of virtual brackets;

(d) inserting the first straight segment of the target custom arch wire into the slot of the first virtual bracket; wherein the first straight segment is designated for insertion into the slot of the first virtual bracket;

(e) selecting a second virtual bracket from the set of virtual brackets; wherein the second virtual bracket is the neighbor of the first virtual bracket;

(f) inserting the second straight segment of the target custom arch wire into the slot of the second virtual bracket; wherein the second straight segment is designated for insertion into the slot of the second virtual bracket; and (g) evaluating the quality of insertion of the second straight segment into the slot of the second virtual bracket.

The above method is then repeated successively for the neighbors in one direction of the first bracket and then in the other direction. When all the evaluation is completed for the entire arch wire, then the total movement of all the straight segments in the arch wire is computed for using it as a criterion for selecting a bracket as a starting point in the arch wire insertion process as described in the next aspect of the invention.

The method is applied for inserting the arch wire in the brackets placed on the teeth of a patient one jaw at a time. For example, the insertion of the arch wire can be evaluated in the lower jaw first, and then the upper jaw, or vice-versa; as the need may be.

As noted earlier, in the case of a collision or conflict, the arch wire design is optimized by modifying the length of the appropriate straight segment, thereby modifying the design of the target arch wire, so as to attempt to remove the collision. However, it is possible that even after such optimization, the collision or the conflict may persist.

It should be noted that the geometry of the target custom arch wire is typically non-planar in three-dimensions.

The results of the wire insertion process in terms of the virtual arch wire and the virtual brackets are continuously displayed to the user In another aspect, a method is provided for selecting the recommended starting point for inserting the virtual arch wire in the virtual brackets in the initial dentition state of the patient. The method identifies the recommended starting point for the arch wire insertion, and simulates and displays the shape of the virtual arch wire after insertion into a non-passive state. Each bracket slot is selected as a starting point, and the process for the virtual arch wire insertion into the virtual brackets is simulated as described above. Finally, the overall results of the arch wire insertion for all starting points are evaluated. From the evaluation, the recommended starting point for the arch wire insertion is determined as follows:

(a) Only one starting point without collisions or conflicts: this bracket slot is recommended as starting point.

(b) Several starting points without collisions or conflicts: the bracket slot requiring the minimum sum of the arch wire actual sliding ways is recommended for start.

(c) No starting point without collisions: the arch wire redesign from the treatment planning perspective is recommended. However, the user is informed of the bracket slot with the minimum arch wire insertion depth into the brackets, and a warning is shown; and the use of the arch wire is left to the user.

The method discussed above is summarized as follows:

The method of determining a recommended starting point for inserting a virtual target custom arch wire into a set of virtual brackets, comprising the steps of:

(a) obtaining a model of a set of virtual of brackets placed up on the virtual teeth of a patient in a jaw in an initial state;

(b) obtaining a virtual model of a target custom arch wire designed to be inserted into the virtual brackets; wherein the custom arch wire comprises alternating sequence of straight segments and bent segments; wherein each of the straight segments is designated to be inserted into the slot of a specific virtual bracket from the set of virtual brackets;

(c) selecting a virtual bracket from the set of virtual brackets as a starting point;

(d) inserting the designated straight segment of the target custom arch wire into the slot of the starting point virtual bracket;

(d) inserting the target custom arch wire successively into the slot of each of the virtual brackets remaining from the set of virtual brackets first on one side of the starting point virtual bracket and then the other side; wherein if at least one bent segment or a portion thereof is unavoidably inserted into a bracket slot, then the arch wire insertion is identified as having collision; and otherwise the arch wire insertion is identified as collision-free;

(e) finding the total movement of the straight segments;

(f) repeating steps (c)-(f) until each of the virtual brackets from the set of virtual brackets has been considered as a starting point virtual bracket; and (g) selecting a starting point virtual bracket having collision-free arch wire insertion and minimal total movement of straight segments as recommended starting points for arch wire insertion.

In yet another aspect a workstation is provided for storing and running the digital simulation software for the arch wire insertion quality check and optimization. The software enables the user to check the insertion quality of the custom arch wire designed during treatment planning phase. When a wire insertion conflict is detected, the software attempts, through the optimization software routine, alternate length configurations for the arch wire straight segment involved in the conflict in order to remove the conflict. If the conflict persists even after the optimization step, then the conflict is shown to the user. In another aspect, the workstation enables a user in determining the best bracket to be used as a starting point in the arch wire insertion process.

The workstation for determining one or more recommended starting points for inserting a virtual target custom arch wire into a set of virtual brackets, comprises:
  a processor;
  a graphical user interface; and
  a computer storage medium;
  wherein said computer storage medium contains:
    (a) a model of a set of virtual of brackets placed up on the virtual teeth of a patient in a jaw in an initial state;
    (b) a virtual model of a target custom arch wire designed to be inserted into the virtual brackets; wherein the custom arch wire comprises alternating sequence of straight segments and bent segments; wherein each of the straight segments is to designated to be inserted into the slot of a specific virtual bracket from the set of virtual brackets; and
    (c) instructions for:
      (i) selecting a virtual bracket from the set of virtual brackets as a starting point;
      (ii) inserting the designated straight segment of the target custom arch wire into the slot of the starting point virtual bracket;
      (iii) inserting the target custom arch wire successively into the slot of each of the virtual brackets remaining from the set of virtual brackets first on one side of the starting point virtual bracket and then the other side; wherein if at least one bent segment or a portion thereof is unavoidably inserted into a bracket slot, then the arch wire insertion is identified as having collision; and otherwise collision-free;
      (iv) finding the total movement of the straight segments;
      (v) repeating steps (i)-(iv) until each of the virtual brackets from the set of virtual brackets has been considered as a starting point virtual bracket; and
    (g) selecting a starting point virtual brackets having collision-free arch wire insertion and minimal total movement of straight segments as recommended starting points for arch wire insertion.

BRIEF DESCRIPTION OF THE DRAWINGS

Presently preferred embodiments of the invention are described below in reference to the appended drawings, wherein like reference numerals refer to like elements in the various views, and in which:

FIG. 3 shows the virtual brackets placed up on the virtual teeth of the patient.

FIG. 4 also shows the various parameters by which the orthodontist can adjust the shape of the arch, the distance between the teeth, the distance between the molars, and other parameters, so as to provide a unique and customized target situation for the patient.

FIG. 12 shows the normal vector Y for a particular bracket, the tangential vector X, the tangential distance $T_d$ and anti-tangential distance $AT_d$.

FIG. 13 shows in matrix form the values for an individual bracket which describe the location of the bracket and its orientation, which are used to generate the commands for the robot to form the orthodontic arch wire.

FIG. 14 is an illustration of a set of points P1, P2, P3, ... PN which represent a set of bending points associated with individual brackets for a patient in a target situation. The location of the points in the three-dimensional coordinate system is known.

DETAILED DESCRIPTION OF PREFERRED EMBODIMENTS

Overview

Figure 1:
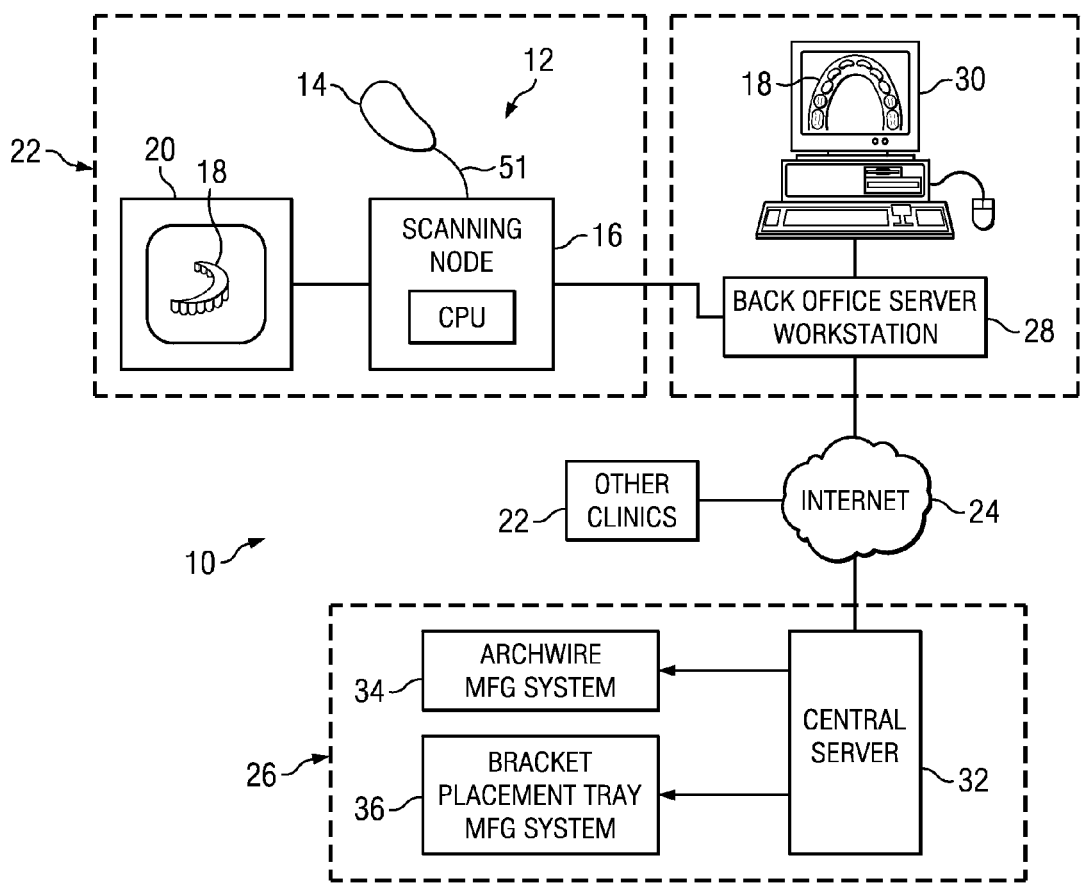
FIG. 1 is an illustration of an orthodontic care system incorporating a hand-held scanner system. The hand-held scanner is used by the orthodontist or the assistant to acquire three-dimensional information of the dentition and associated anatomical structures of a patient and provide a base of information to diagnose and plan treatment for the patient.

FIG. 1 is an illustration of an orthodontic care system 10 incorporating a scanner system 12. The scanner system 12 includes a hand-held scanner 14 that is used by the orthodontist or his assistant to acquire three-dimensional information of the dentition and associated anatomical structures of a patient. The images are processed in a scanning node or workstation 16 having a central processing unit, such as a general-purpose computer. The scanning node 16, either alone or in combination with a back-office server 28, generates a three-dimensional computer model 18 of the dentition and provides the orthodontist with a base of information for diagnosis, planning treatment, and monitoring care for the patient. The model 18 is displayed to the user on a monitor 20 connected to the scanning node 16.

As noted above, the scanner system 12 is optimized for in-vivo scanning of teeth, or alternatively, scanning a plaster model of the teeth and/or an impression of the teeth.

The orthodontic care system consists of a plurality of orthodontic clinics 22 which are linked via the Internet or other suitable communications medium 24 (such as the public switched telephone network, cable network, wireless network, etc.) to a precision appliance service center 26. Each clinic 22 has a back office server work station 28 having its own user interface, including a monitor 30. The back office server 28 executes an orthodontic treatment planning software program. The software obtains the three-dimensional digital data of the patient's teeth from the scanning node 16 and displays the model 18 for the orthodontist. The treatment planning software includes features to enable the orthodontist to manipulate the model 18 to plan treatment for the patient. For example, the orthodontist can select an archform for the teeth and manipulate individual tooth positions relative to the archform to arrive at a desired or target situation for the patient. The software moves the virtual teeth in accordance with the selections of the orthodontist. The software also allows the orthodontist to selectively place virtual brackets on the tooth models and design a customized virtual arch wire for the patient given the selected bracket positions. Alternately, a scan may be taken of the patient's dentition with the brackets already placed on the patient's teeth. In this case a virtual model is created from the scan data, using the system 10 software which may be placed in the scanning node 16, the back office server work station 28 or the central server 32, such that the teeth and the brackets can be manipulated as individual virtual objects. In this case the practitioner or the user designs the customized arch wire using the positions of the brackets as those already placed on the patient's teeth. When the orthodontist has finished designing the orthodontic appliance for the patient, digital information regarding the patient, the malocclusion, and a desired treatment plan for the patient is sent over the communications medium to the appliance service center 26. A customized orthodontic arch wire and a device for placement of the brackets on the teeth at the selected location is manufactured at the service center and shipped to the clinic 22.

As shown in FIG. 1, the precision appliance service center 26 includes a central server 32, an arch wire manufacturing system 34 and a bracket placement manufacturing system 36. For more details on these aspects of the illustrated orthodontic care system, the interested reader is directed to the patent application of Rüdger Rubbert et al., filed Apr. 13, 2001, entitled INTERACTIVE AND ARCHWIRE-BASED ORTHODONTIC CARE SYSTEM BASED ON INTRA-ORAL SCANNING OF TEETH, Ser. No. 09/835,039, now issued as U.S. Pat. No. 6,648,640, the entire contents of which are incorporated by reference herein.

A virtual model of the dentition of the patient is created through scanning. This may be done through in-vivo scanning of the patient, or through scanning of the physical model of the patient. Individual virtual tooth objects are created from the virtual dentition model. The digital models of the brackets, arch wires and other orthodontic appliances can be stored in the workstation storage in the form of libraries, and retrieved during treatment planning as needed. The digital models of the brackets can be created from scanning individual brackets. Often, scanning of the patient's dentition is done where the brackets are already mounted on the patient's teeth. In this case, the virtual model comprises individual virtual tooth objects and individual virtual bracket objects. The combination of the displayed set of virtual orthodontic brackets, together with the virtual orthodontic arch wire, presents to the user a customized virtual orthodontic appliance. The virtue of the customized virtual orthodontic appliance is that it can be studied, modified, shared between two computers, and transported electronically over a communications medium for fabrication of the orthodontic appliance. The treatment planning software is essentially a specialized CAD/CAM system that allows the design of virtually any configuration of tooth objects, bracket objects, wire objects and other appliances and objects. Because these objects exist as independent mathematical objects, they can be selectively displayed together or alone. For example, the treatment planning software displays an icon or button on the user interface that allows the user to select or deselect the teeth, wires, brackets or virtual objects or appliances, as desired. For example, the teeth and arch wire can be displayed together with the brackets deleted from the user interface. The orthodontist can then select an individual tooth object, move it in three dimensions, and the movement of the tooth carried over to a repositioning of the bracket in three dimensions and a changing of the shape of the arch wire.

Furthermore, while the above process of creation of tooth models has been described in conjunction with the scan data from the hand-held scanner, this is not required. The separation of tooth objects can be performed with any three-dimensional model of the teeth, regardless of how the three-dimensional model is obtained. The three-dimensional model could be acquired from a CT scan, a laser scan from a plaster impression, or otherwise.

Treatment Planning

The virtual model of the patient's dentition, and the individual tooth objects created as explained above, provide a base for diagnostic analysis of the dentition and treatment planning Treatment planning software is provided on the workstation of the orthodontic clinic, and possibly at other remote locations such as the precision appliance center of FIG. 1. The treatment planning software can be considered an interactive, computer-based computer aided design and computer aided manufacturing (CAD/CAM) system for orthodontics. The apparatus is highly interactive, in that it provides the orthodontist with the opportunity to both observe and analyze the current stage of the patient's condition, and to develop and specify a target or desired stage. A shortest direct path of tooth movement to the target stage can also be determined. Further, the apparatus provides for simulation of tooth movement between current and target stages. For further details on treatment planning, refer to the previously mentioned patent application of Rüdger Rubbert et al., filed Apr. 13, 2001, entitled INTERACTIVE AND ARCHWIRE-BASED ORTHODONTIC CARE SYSTEM BASED ON INTRA-ORAL SCANNING OF TEETH, Ser. No. 09/835,039, now issued as U.S. Pat. No. 6,648,640, the entire contents of which are incorporated by reference herein.

Figure 2:
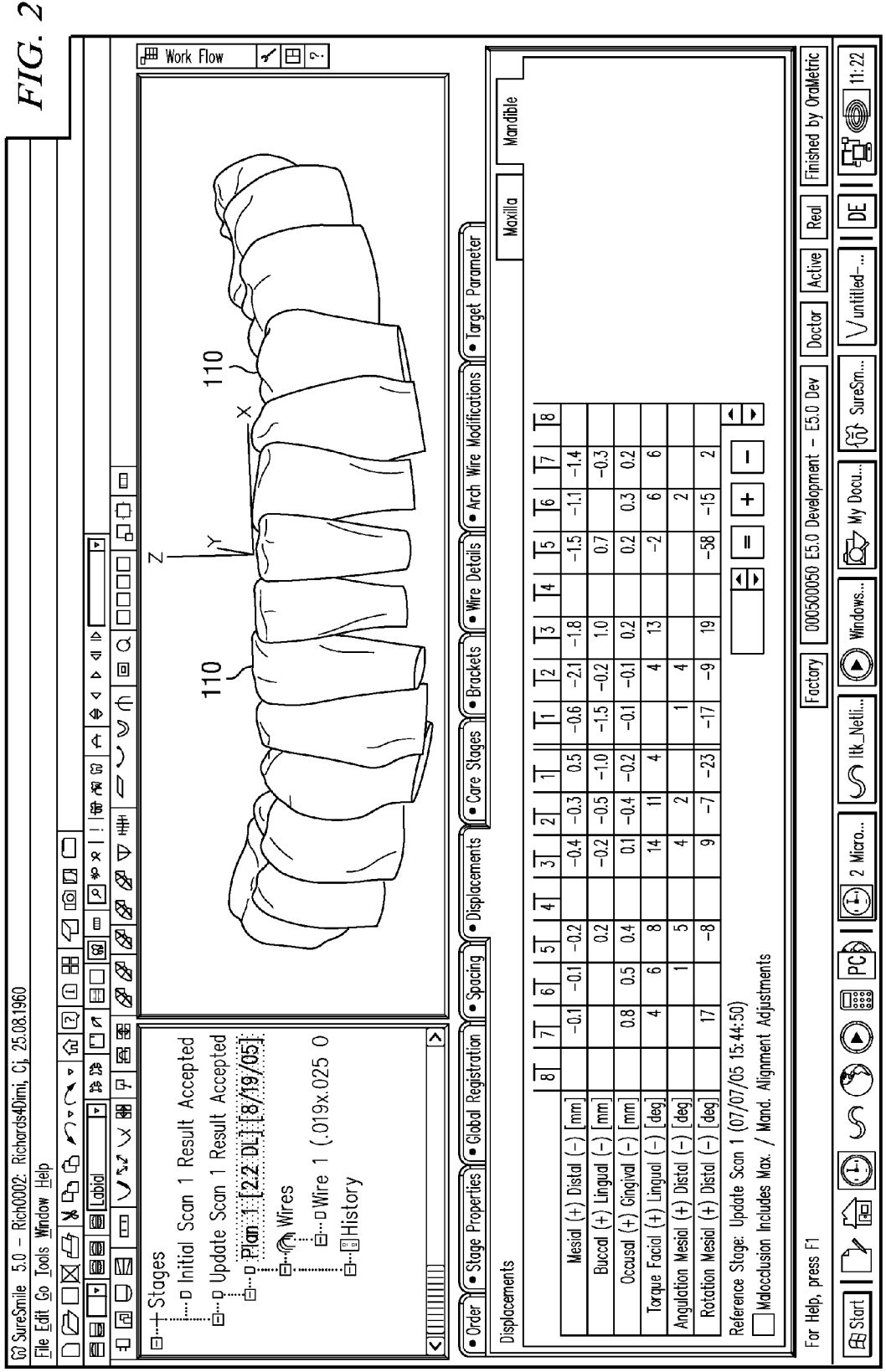
FIG. 2 is a screen shot showing the virtual model of the teeth of a patient in malocclusion state.

FIG. 2 is a screen shot showing the virtual model of the teeth 110 of a patient in malocclusion state.

Figure 3:
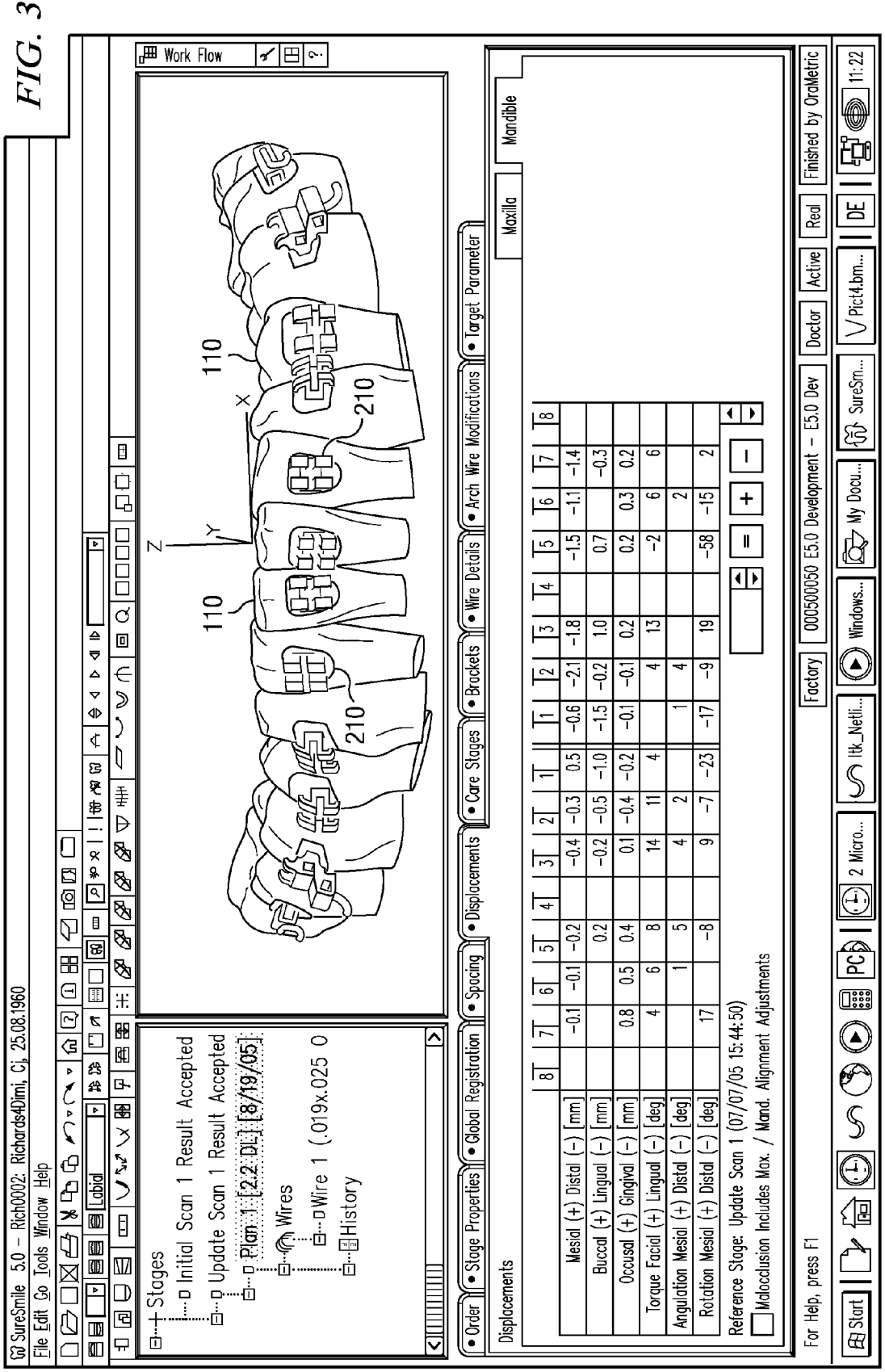
FIG. 3 is a screen shot of the virtual model of the teeth of a patient in the malocclusion state the same as in FIG. 2. Additionally.

FIG. 3 is a screen shot of the virtual model of the teeth 110 of a patient in the malocclusion state the same as in FIG. 2. Additionally, FIG. 3 shows the virtual brackets 210 which are placed up on the virtual teeth 110 of the patient. The placement of the virtual brackets on the virtual teeth can be as a result of the treatment planning using the software provided in the system 10 of FIG. 1. Alternately, the placement of the virtual brackets on the virtual teeth can be obtained through the scanning of the patient's dentition where the practitioner has already placed the brackets up on the teeth of the patient.

Figure 4:
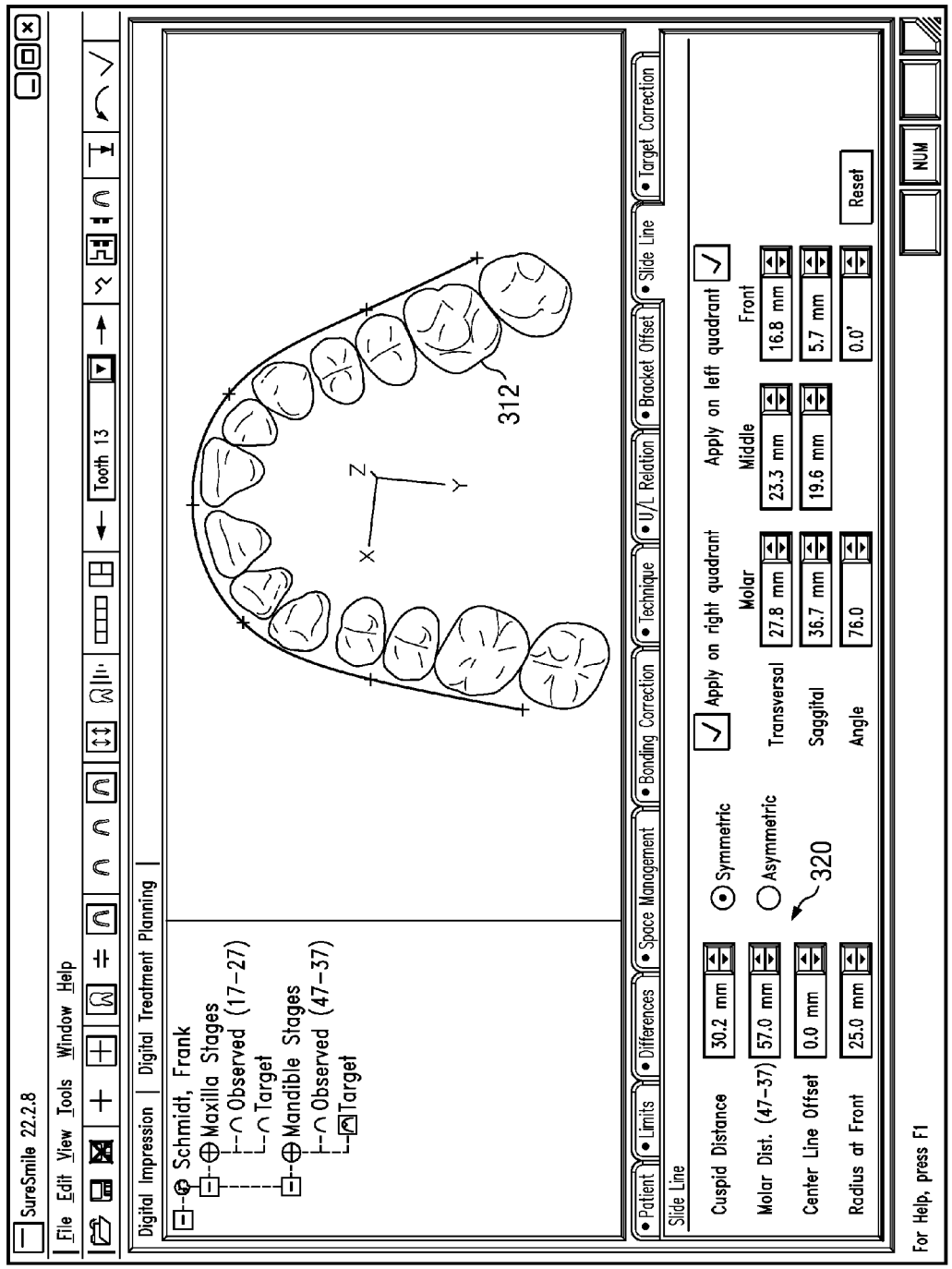
FIG. 4 is a screen shot from an orthodontic workstation showing the computer model of the patient's teeth positioned in a target or desired condition.
Figure 5:
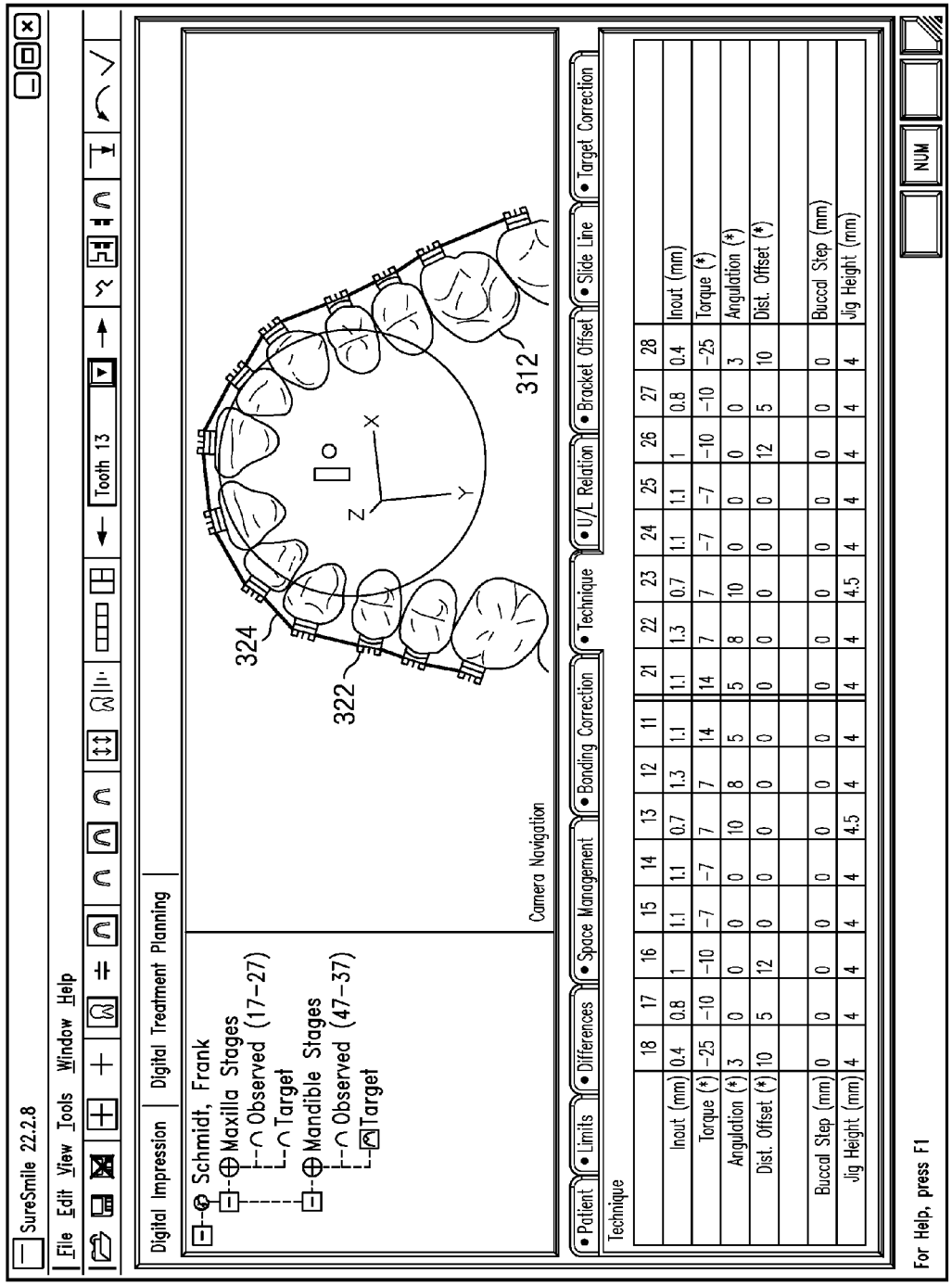
FIG. 5 is another screen shot showing the computer model of the patient's teeth in a target situation, also showing the numerous parameters available to the orthodontist to customize the tooth position, orientation, angulation, torque, and other parameters on a tooth by tooth basis for the target archform.

FIG. 4 is a screen shot from an orthodontic workstation showing the computer model of the patient's teeth objects 312 positioned in a target or desired condition. The illustration is the result of the user selecting an archform for the patient from a known type of archform (e.g., Roth), and the computer placing the teeth along the arch selected by the user. This is executed by placing the virtual brackets the orthodontist placed on the virtual teeth along the curve selected by the orthodontist. The brackets are omitted from FIG. 4, but are shown in FIG. 5. The software allows the orthodontist to change many variables in the target situation, simply by entering new values in the slide line area 320 of the screen display, by mouse operation of up and down arrows to scroll through available values, or by mouse operation of a bar to change the values, or other similar technique. FIG. 4 shows some of the parameters by which the orthodontist can adjust the shape of the arch, the distance between the teeth, the distance between the molars, and other parameters, so as to provide a unique and customized target situation for the patient.

FIG. 5 is another screen shot showing the computer model of the patient's teeth in a target situation, also showing the numerous parameters available to the orthodontist to customize the tooth position, orientation, angulation, torque, and other parameters on a tooth-by-tooth basis for the target archform. Virtual brackets 322 are positioned on the tooth objects 312 at the location where the user placed the landmarks. A virtual arch wire 324 passes through the slots in each virtual bracket.

Figure 6:
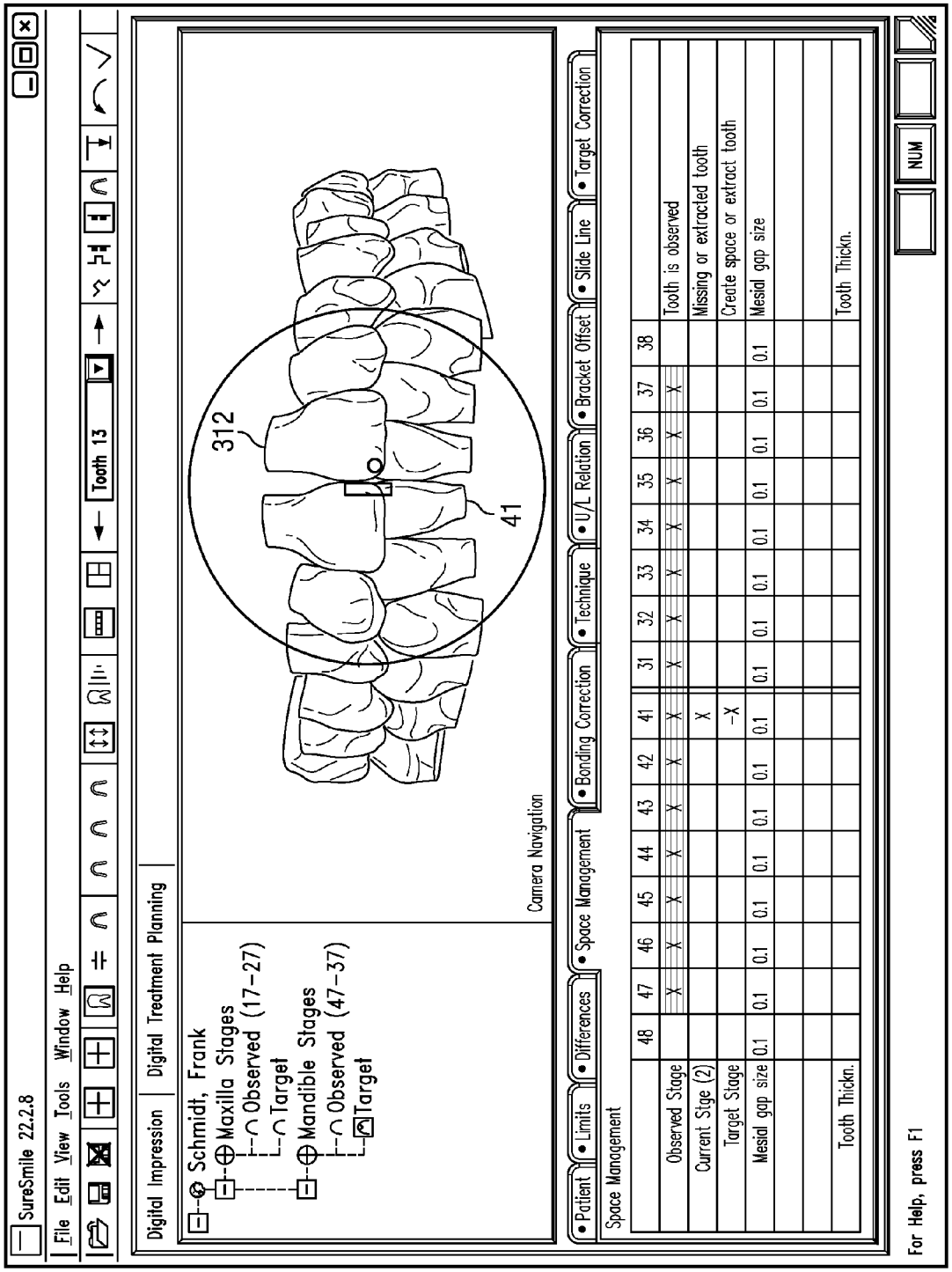
FIG. 6 is another screen shot showing a front view of the target situation and additional parameters available to the orthodontist for moving teeth relative to each other in planning treatment for the patient.

FIG. 6 is another screen shot showing a front view of the target situation and additional parameters available to the orthodontist for simulating the movement and positioning of teeth relative to each other in planning treatment for the patient. For example, in FIG. 6, the cursor is moved onto the virtual tooth 41 (in the tooth numbering convention) and the mouse is clicked. Tooth 41 is then highlighted. If the orthodontist wants to extract that tooth, then the tooth could be extracted in the simulation. Alternatively, tooth 41 could be rotated about any of three axis of rotation, moved in the X, Y or Z direction, or a larger or smaller gap could be created between teeth.

Figure 7:
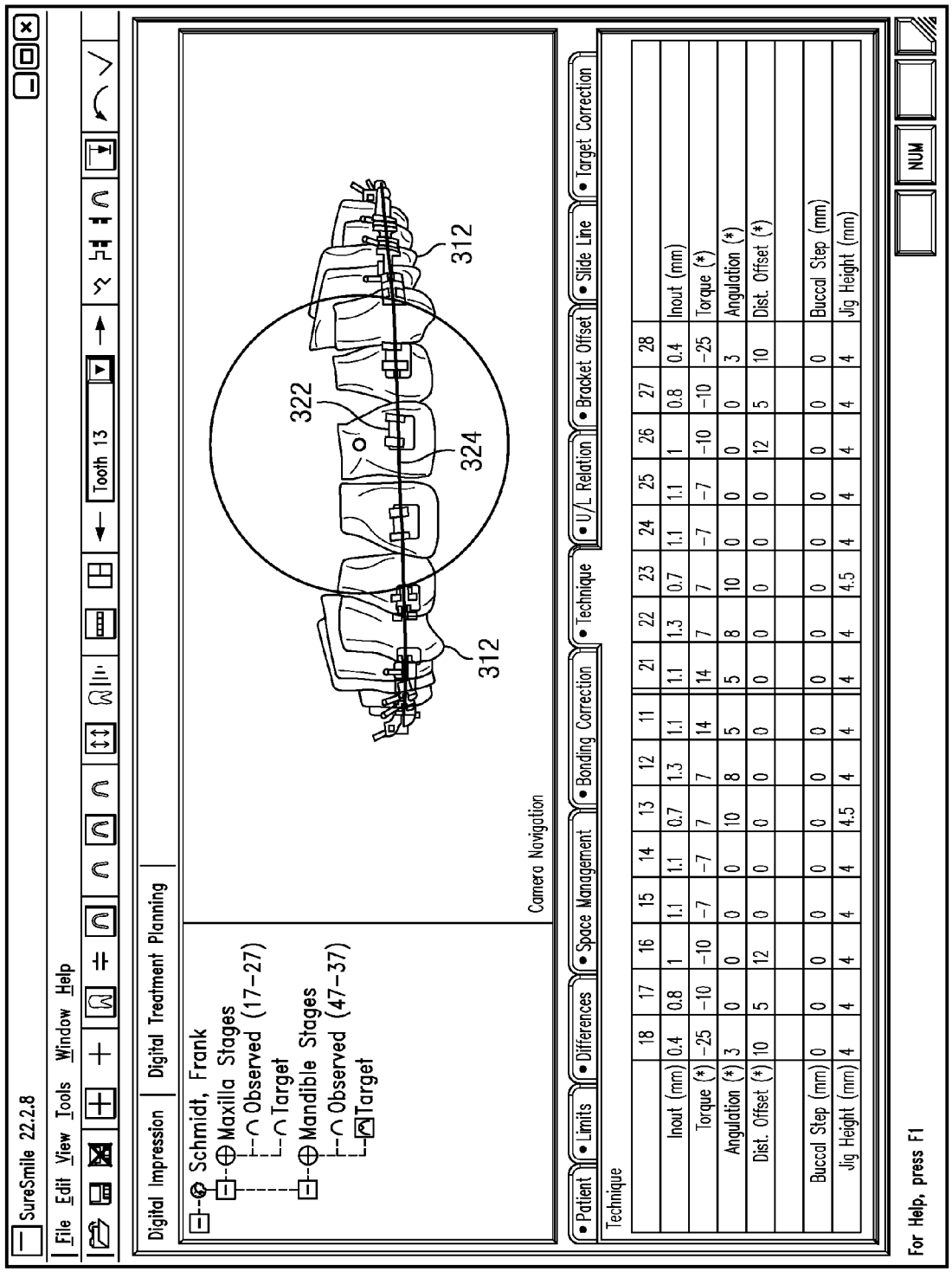
FIG. 7 is a screen shot of a target situation for the patient showing the virtual tooth in a target position, a set of virtual brackets placed on the teeth, and a virtual arch wire.

FIG. 7 shows the target situation for the upper arch, with the virtual brackets 322 in place. The orthodontist can adjust the bracket 322 position, arch wire shape 324, or tooth 312 position, on a tooth by tooth basis to thereby optimize treatment planning for the patient.

The result of the treatment planning is the generation of a set of bracket placement positions, if already not given, and the display on the monitor of the shape of a customized orthodontic arch wire to treat the malocclusion.

Arch Wire Design

The arch wire design, which dictates the shape of an arch wire resulting from the treatment planning, will now be discussed in conjunction with FIGS. 8-15. The arch wire design includes a set of matrices, one matrix for each bracket in the arch of the patient. Each matrix consists of a combination of a vector of location of a point on the bracket and a matrix of orientation, indicating the orientation of the bracket in three-dimensional space. Both the vector of location and the matrix of orientation are based on the position of the brackets on the teeth when the teeth are in a target situation. The target situation is developed by the orthodontist from the scan of the dentition and the execution of a treatment planning using the treatment planning software at the clinic.

Figure 8:
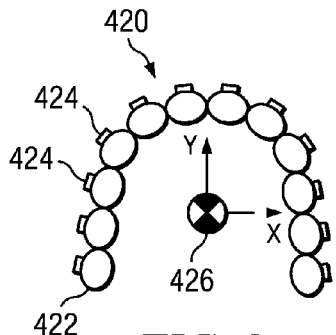
FIG. 8 is a simplified illustration of a set of teeth showing the origin of a coordinate system that is used to calculate bracket location for a set of brackets, in three dimensions, for a patient. The bracket location for the teeth in a target situation determines the shape of an orthodontic arch wire.

FIG. 8 illustrates the target situation for one arch 420 of a patient. The target situation is a three dimensional virtual model of the teeth 422 in which virtual brackets 424 are placed, for example, on the labial surface of the teeth. A coordinate system is defined for the arch 420 having an origin 426. The coordinate system is in three dimensions, with the X and Y dimensions lying in the plane of the arch and the Z direction pointing out of the page. The location of the origin 426 is not particularly important. In the illustrated embodiment, an average "mass" is assigned to each virtual tooth in the arch, and a center of "mass" is calculated for the arch 420 and the original 426 is located at that center.

Figure 9:
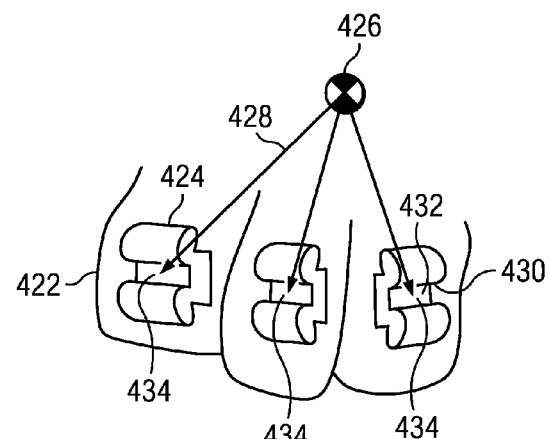
FIG. 9 is an illustration showing the vectors drawn from the origin of the coordinate system to the center of the brackets.
Figure 10:
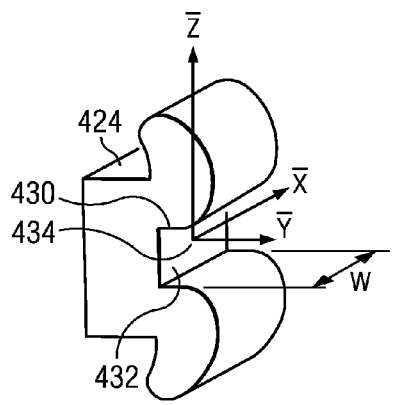
FIG. 10 is a perspective view of an orthodontic bracket.

As shown in FIGS. 9 and 10, a vector of location 428 is defined for each bracket. The vector 428 extends from the origin 426 to the center of the slot 430 in the bracket along the wall 432 of the bracket slot, i.e., to point 434. The vector of location consists of the X, Y and Z coordinates of the point 434 in the defined arch coordinate system.

The orientation matrix consists of a 3×3 matrix of unit vectors of the form:

$$\begin{matrix} X_1 & Y_1 & Z_1 \\ X_2 & Y_2 & Z_2 \\ X_3 & Y_3 & Z_3 \end{matrix} \quad 1)$$

where $X_1$, $X_2$ and $X_3$ are the X, Y and Z components of the X unit vector shown in FIG. 10; $Y_1$, $Y_2$ and $Y_3$ are the X, Y and Z components of the Y unit vector shown in FIG. 10; and $Z_1$, $Z_2$ and $Z_3$ are the X, Y and Z components of the Z unit vector shown in FIG. 10. As noted above, the matrix for each bracket thus consists of the combination of the 3×3 orientation matrix and the position matrix, and is thus as follows:

$$\begin{matrix} X_1 & Y_1 & Z_1 & X \\ X_2 & Y_2 & Z_2 & Y \\ X_3 & Y_3 & Z_3 & Z \\ 0 & 0 & 0 & 1 \end{matrix} \quad 2)$$

where X, Y and Z in the right hand column of entries is the position vector.

The arch wire design also includes an antitangential value and a tangential value for each bracket. The antitangential value consists of the distance from the center of the bracket slot (point 434) to a point defining the terminus of the previous bend in the wire. The tangential value consists of the distance from the center of the bracket slot to the point defining the terminus of the next bend in the wire. The arch wire design also consists of the thickness of the wire, as measured in the direction of the Y unit vector in FIG. 10.

Figure 11:
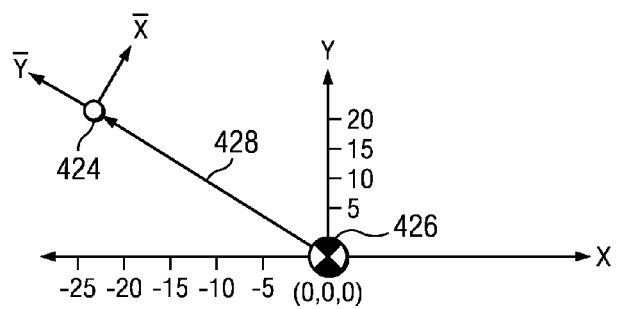
FIG. 11 shows the origin, the position vector, and the X and Y unit vectors which indicate the orientation of the bracket slot. It also shows the scale (in units of millimeters) which gives absolute location and orientation information for the bracket slot.
Figure 15:
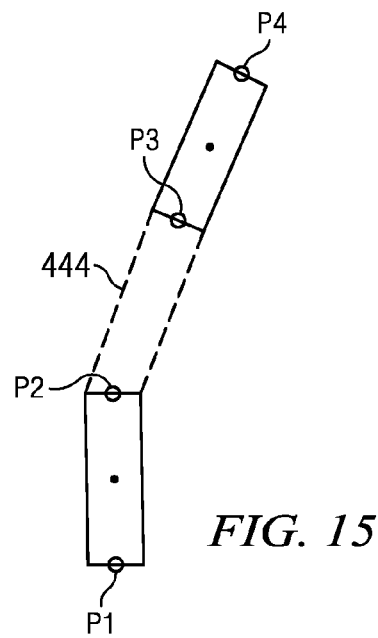
FIG. 15 is an illustration of a section of wire between points P1 and P4 in which a bend is placed between points P2 and P3.

With reference to FIG. 11, an example of the 4×4 matrix 2) for a rear most molar of a patient will be described. Figure shows the origin 426, the position vector 428, and the X and Y unit vectors which indicate the orientation of the bracket slot. FIG. 11 also shows the scale (in units of millimeters) which gives absolute location and orientation information for the bracket slot. Here, we assume in the example that there is no Z component to the tangential vector X or the normal vector Y.

FIG. 12 shows the tangential distance $T_D$ and the antitangential distance $AT_D$ as measured along the centerline of the arch wire. The resulting matrix is shown in FIG. 13.

From a set of the matrices as shown in FIG. 13 comprising all the brackets in the arch, the program extracts a series of line segments in three dimensional space, which are defined by the terminus of the antitangential and tangential distances for each bracket slot. The set of line segments 440 is shown in FIG. 14. The line segments are defined by a set of points P1, P2, P3 ... Pn having known three dimensional coordinates due to the known location of the bracket slots and the known tangential and antitangential distances. The line segments can also be defined as a set of vectors having a location for the head of the vector and a magnitude and orientation in three directions. The following discussion will use the set of points P1, P2, P3 ... PN. In FIG. 14, the slashes 442 indicate the end points of the bracket slot 430 of FIG. 10.

The bends need to be placed in the wire before point P1, between points P2 and P3, between points P4 and P5, etc., that is, between the bracket slots. The slot-to-slot bends of the complete arch wire are bent section by section. The straight wire sections 440 between the bends have to fit to the bracket slots. The bend is indicated at 444 in FIG. 15. Once the arch wire design is complete from the treatment planning view point, it is subjected to the insertion quality check, and further optimization if necessary, as described below.

Arch Wire Insertion Evaluation and Design Optimization

Prior to actually manufacturing the target arch wire designed above through treatment planning, it is important to check if the target virtual arch wire could be inserted into the virtual brackets placed on the virtual dentition of the patient in the initial state of interest without conflicts or collisions. As noted earlier the customized arch wire consists of alternating sequence of straight segments and custom bent segments. Customized bends may comprise bends and twists, which may be complex and typically make the arch wire shape non-planar. Straight segments are designed to go in the bracket slots and the bent segments between the brackets. If during the arch wire insertion process, if the wire cannot be inserted into a bracket slot without keeping a portion of the bet segment out of the bracket slot, then a conflict or a collision is created. In other words, the arch wire insertion where a portion of a bent segment gets in the bracket slot is called a conflict or a collision. One or more conflicts diminish the effectiveness of the arch wire in moving the teeth from malocclusion to the target positions. The initial state might be the malocclusion state or an intermediate state during the course of the treatment. Without the loss of generality, the following discussion will primarily assume the initial state to be the mal occlusion state. In the event the target virtual arch wire would cause conflicts violating the effectiveness of the designed target arch wire, then it is important to know the location and extent of the conflicts so that corrective options to remove the conflicts can be evaluated and exercised as and when appropriate so as to optimize the design of the arch wire. The instant invention provides these capabilities. The instant invention provides the capabilities to indicate and visualize conflicts for the whole arch wire and on the level of individual brackets, so that further judgments and measurements can be applied easily. The instant invention reliably indicates "no conflict" or "possible conflicts". That means automated judgment regarding "conflict free insertion" or indication of needed attention to solve the conflicts through alternate and optimized design of the target arch wire. Furthermore, in a preferred embodiment, the invention calculates and shows a recommended starting point for the arch wire insertion, and simulates and displays the shape of the virtual arch wire after insertion into a non-passive state.

As discussed above, in order to achieve the treatment objective, the arch wire is bent in a manner such that it comprises alternating straight segments and bent segments. When the target arch wire is ligature tied to the bracket slots, it enables, in the relaxed state, movement of the teeth to the target positions. A preferred embodiment of the invention digitally simulates the insertion of the virtual arch wire into the virtual brackets placed up on virtual teeth of a patient in malocclusion or any initial state of interest. The digital simulation takes into account the following requirements and constraints that would be applicable with respect to the actual arch wire when inserted into the actual brackets bonded to the patient's teeth. The ligature tying of the arch wire to the brackets placed on the patient's teeth in the malocclusion state (or any other state of interest) should be done in such a way that the arch wire may conduct the necessary movements during the course of the treatment while satisfying the following conditions. When ligature tying the arch wire, each straight part of the arch wire has to be placed in the designated bracket slot in the malocclusion or initial state. In addition, the arch wire must be able to move during the course of the treatment to such a distance that the target teeth position can be reached without having the arch wire getting stuck or interlocked within or at the edges of the brackets. As described earlier, these straight wire parts or segments are incorporated into the arch wire design, and have lengths per the target arch wire design resulting from the treatment planning.

According to a preferred embodiment of the invention, computer software for the arch wire insertion quality check, and the arch wire design alteration and optimization when necessary, is provided in the central server 32 of FIG. 1. However, one skilled in the art would appreciate that this simulation software can as well be placed in the back office server workstation 28, the scanning node 16 or any other workstation in the system 10. One of the tasks of the simulation software routine described herein is to simulate the ligature tying of the virtual arch wire and to check whether the designed virtual arch wire can be ligature tied to the brackets under the given constraints. In summary, the essential steps carried out by the simulation software are: (a) the numerical calculation of the deformation of the virtual arch wire or the arch wire segments between the bracket slots, and (b) the determination of the resulting relative positions of the straight segments or the actual sliding ways with respect to the brackets at the malocclusion and the realization of a balance between the segments by shifting the arch wire along the bracket slots within the tolerable range. The arch wire of the target stage designed as previously described serves as the basis or the starting point for the insertion quality check and optimization. This arch wire is represented by a sequence of segments. These segments are an alternating sequence of straight parts or segments and parts having bends, twists or complex bends which may be specified according to a Bezier spline. All of the arch wire segment lengths used in simulation initially exactly match the wire design described earlier. The arch wire design is represented in the form of a data file. When the arch wire is manufactured, this data file in its final form after the insertion check and optimization simulation guides the robot, which bends the arch wire in the desired shape. The insertion simulation takes into account elastic and pseudoplastic deformations of the wire.

Figure 16:
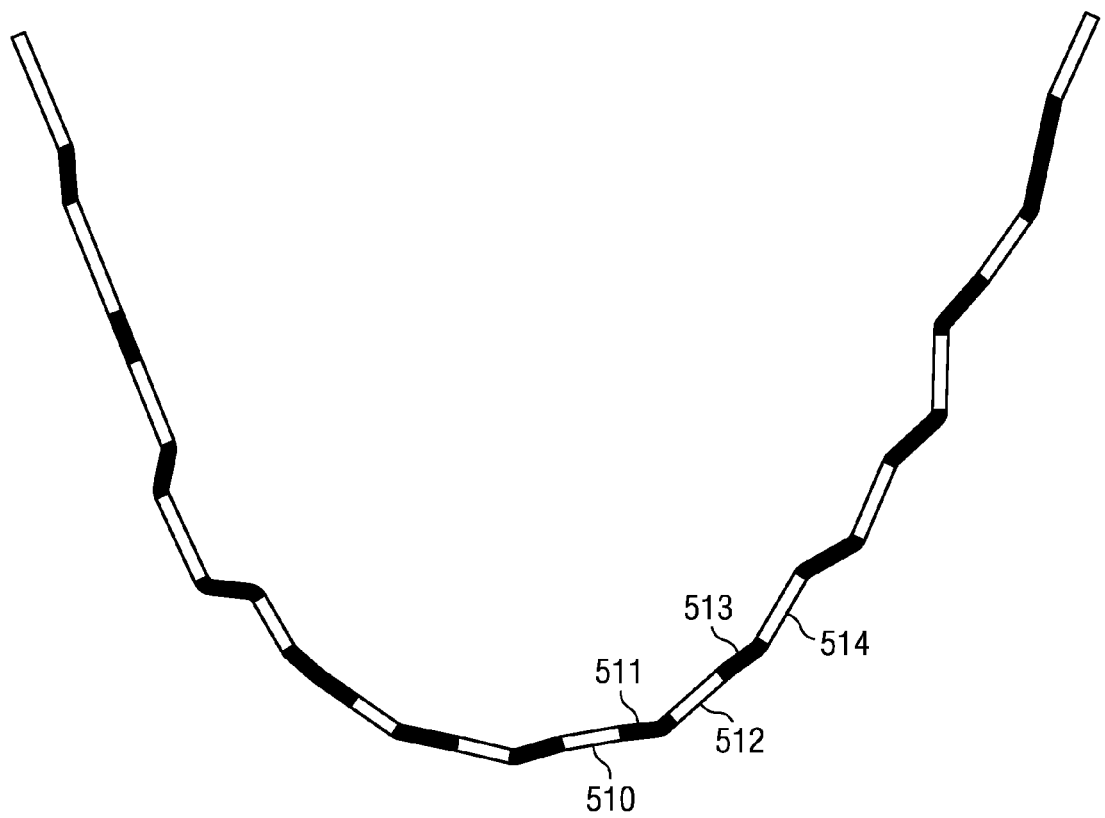
FIG. 16 shows the arch wire designed for the target state through treatment planning.

FIG. 16 shows a virtual arch wire designed for the target state per the treatment planning described earlier. The virtual target arch wire in FIG. 16 comprises alternating straight segments (e.g. straight segments 510, 512 and 514) and bent segments (e.g. bent segments 511 and 513). There is one straight segment per bracket, and each straight segment is designated for insertion into a specific bracket slot.

Figure 17:
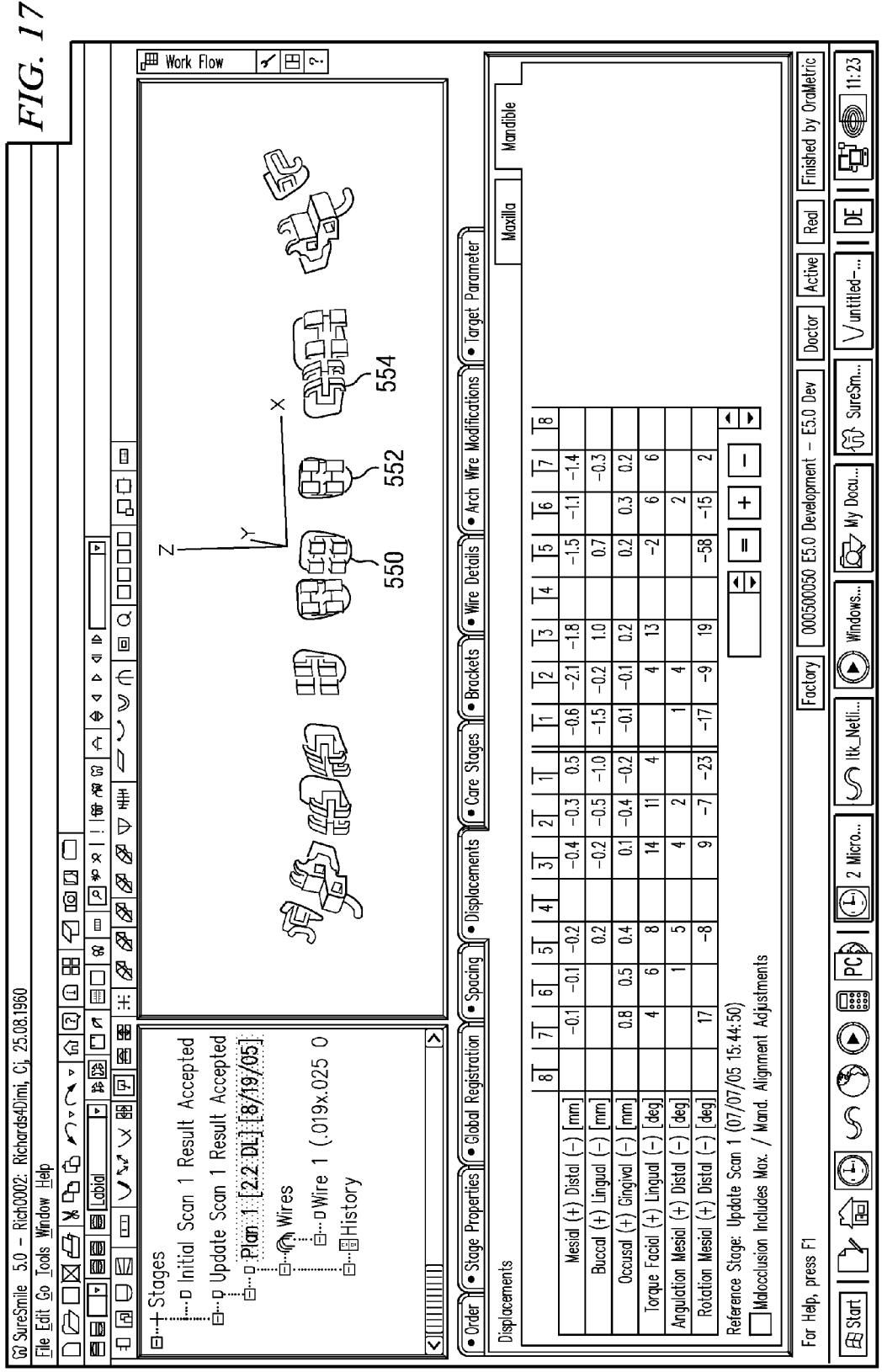
FIG. 17 shows a version of FIG. 3 where simply the virtual brackets are shown placed in the malocclusion state the same as in FIG. 3, and the virtual teeth are hidden from the view.

FIG. 17 shows a modified view of the screen shot in FIG. 3. FIG. 17 shows the virtual brackets (e.g. the virtual brackets 550, 552 and 554) (the virtual brackets 210 in FIG. 3) placed in the malocclusion state of the patient. The virtual teeth (the virtual teeth 110 in FIG. 3) are hidden from the view in FIG. 17.

Figure 18:
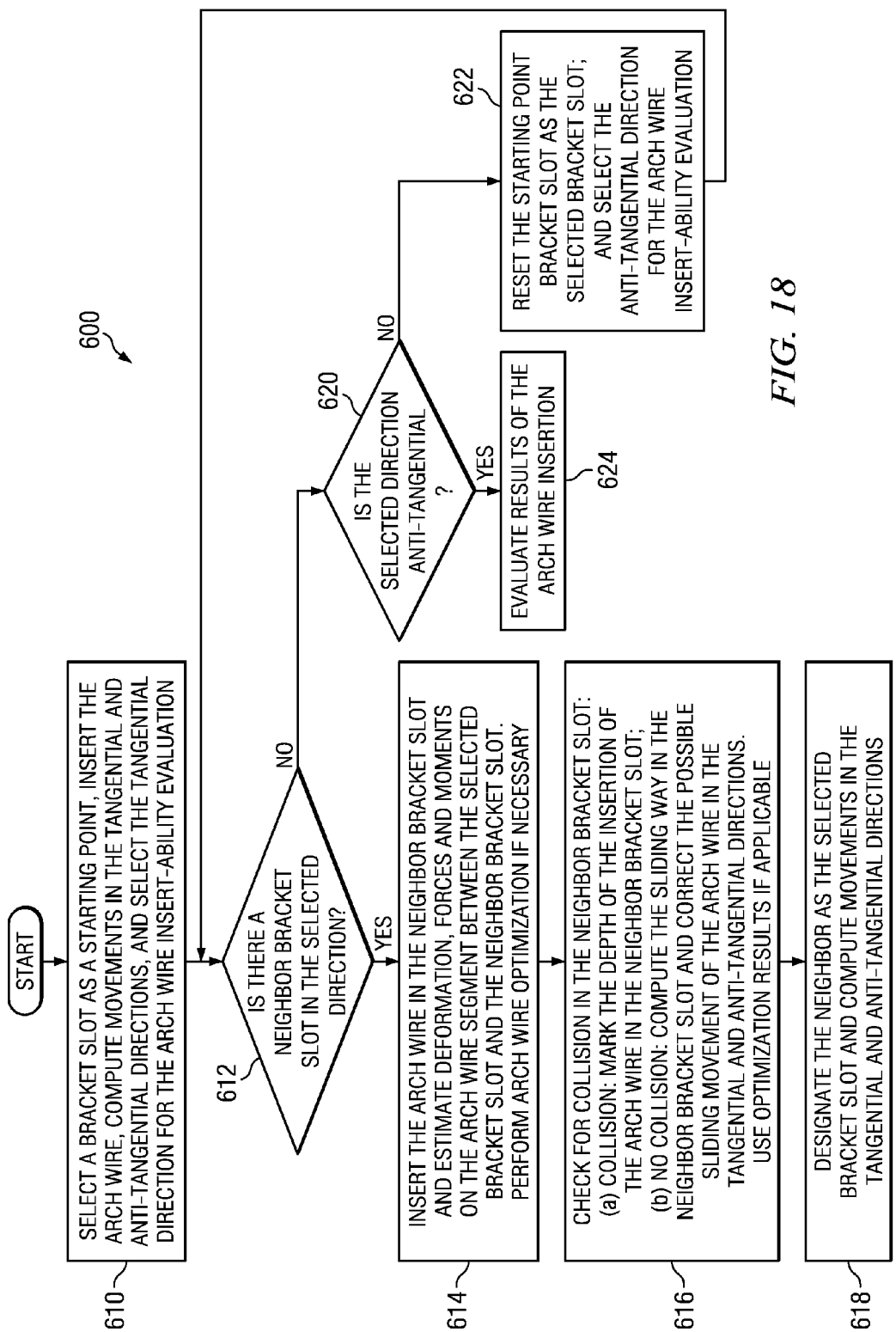
FIG. 18 shows a flow chart for carrying out the virtual arch wire insertion check and optimization simulation, according to a preferred embodiment of the invention. The simulation process is iterative.

FIG. 18 shows a flow chart 600 for carrying out the virtual arch wire insertion quality check and the arch wire optimization simulation according to a preferred embodiment of the invention. The simulation process is iterative.

At step 610, a virtual bracket slot is selected as a starting point, e.g. the slot on the virtual bracket 550 in FIG. 17. This may be a user selected virtual bracket slot, or alternately, automatically selected by the simulation software. Then, the straight segment of the virtual arch wire, e.g. the straight segment 510 in FIG. 16, designated for the selected bracket slot is inserted into the selected bracket slot; and the possible movements of the virtual arch wire in the tangential and antitangential directions are computed. The insertion of the straight segment of the virtual arch wire in the selected virtual bracket slot is done in a manner such that it digitally simulates the ligature tying of the virtual arch wire to the selected virtual bracket slot which permits sliding movements of the virtual arch wire within the selected virtual bracket slot, but prevents the virtual arch wire from popping out of the selected virtual bracket slot. Then, the tangential direction is selected for the arch wire insertion evaluation. The selection of the tangential direction for further evaluation is arbitrary at this point. One can also start the evaluation process by initially selecting the antitangential direction.

Next, at step 612, a check is made to determine if there is a neighbor bracket slot in the selected direction? If the answer at step 612 is in the affirmative, then the process moves to step 614; otherwise to step 620.

At step 614, the virtual arch wire, e.g. the straight segment 512 in FIG. 16, is inserted in the virtual neighbor bracket slot, e.g. the slot on the virtual bracket 552 in FIG. 17; and estimates are made of the deformation, the forces and the moments on the virtual arch wire segment between the selected bracket slot and the neighbor bracket slot. The force and moment are required to bring the unrestrained virtual arch wire into an alignment with the virtual neighbor bracket slot. The force is applied incrementally depending up on the distance between the selected and the neighbor virtual brackets and the distance from the virtual arch wire end (in the direction of the neighbor bracket) to the virtual neighbor bracket. The magnitude of the force and the moment and the point on the virtual arch wire where the force is applied, which mimic insertion of the actual arch wire into the actual bracket slot, are calculated incrementally and iteratively.

The initial force is calculated using Eq. (1).

$$\vec{F} = \frac{2 * \vec{D}}{(L/10.0)^2}; \quad \text{Eq. (1)}$$

where:

$\vec{F}$—force;

$\vec{D}$—distance from the virtual arch wire end (in the direction of the neighbor virtual bracket) to the neighbor virtual bracket; and L—length of the virtual arch wire between the two virtual brackets.

Then, the virtual arch wire distortion under the applied force and moment is determined and their (force and moment) value and direction are corrected with the new distance of the unrestrained virtual arch wire end to the target. The new value of the force from the previous value is computed using Eq. (2).

$$\vec{F}_{n+1} = \vec{F}_n + \vec{d} \cdot \frac{\|\vec{F}_n\|}{\|\vec{D}_n\|} \cdot \gamma; \quad \text{Eq. (2)}$$

where:

$\vec{F}_n$—force at the incremental step n;

$\vec{F}_{n+1}$—new force at the incremental step n+1;

$\vec{D}_n$—movement of virtual arch wire under $\vec{F}_n$;

$\vec{d}$—actual distance from the virtual arch wire end (in the direction of the neighbor virtual bracket) to the neighbor virtual bracket;

$\gamma$—damping factor to avoid overshooting; $0<\gamma<1.0$.

During the force and moment calculation it is assumed that the forces at the brackets have only normal component. Then, the force and moment directions are corrected accordingly as the incremental force is applied.

In order to calculate the elastic deformation from the applied force and moment, a linear bending theory is used. The displacement of the point where the force is applied is calculated from an integration of the displacement of the wire cross section over the length of the wire segment. The displacement at a given point results from the locally exerted forces per Eq. (2). where large moments are exerted, it follows a large curvature of the virtual arch wire, and with smaller moments a proportionate smaller one.

The advantage of the incremental and iterative approach is that the pseudo-plastic deformations of the virtual arch wire segment can also be easy accounted for in the simulation. Therefore, above an empirically determined limit of material tension, the affected areas of the virtual arch wire do not react with further force or moment increase to further deformation. Pseudo-plastic deformation plays an important role with the NiTi arch wires.

According to a preferred embodiment of the invention, in order to calculate the deformation from the local moment exerted on the virtual arch wire cross-section (forces may be neglected), the moment is decomposed into three parts: a torsional moment and two bending moments along the main axis. An independent description of these three moments is possible for purely elastic deformations. The deformation can also be expressed using the three angles representing the movement of the arch wire cross section. These angles are calculated from the following equations:

$$\alpha_x = \frac{M_x \cdot h}{I_x \cdot E}; \quad \text{Eq. (3)}$$

$$\alpha_y = \frac{M_y \cdot h}{I_y \cdot E}; \quad \text{Eq. (4)}$$

$$\alpha_z = \frac{M_z \cdot h}{I_z \cdot G}; \quad \text{Eq. (5)}$$

where:

Mx, My—Bending moments;

Mz—Torsional moment;

Ix, Iy, Iz—Moment of inertia of the area in the respective directions;

h—Thickness of the cross section of the virtual arch wire;

E—modulus of elasticity; and

G—modulus of transverse elasticity.

The incremental process of applying the force is stopped if the designated virtual arch wire straight segment is aligned with the corresponding virtual bracket slot within a given tolerance. That means the designated straight segment of the virtual arch wire is be properly inserted into the virtual bracket slot without conflict or collision. On the other hand, even after applying the sufficient force, the arch wire insertion in the neighbor causes a conflict or a collision, then the optimization step is performed where by the length of the straight segment designated for the neighbor bracket slot is modified, i.e. increased or decreased, to see if the conflict or the collision can be removed. It may be recalled that a conflict or a collision is created when a portion of a bent segment gets inserted into a bracket slot during the arch wire insertion process. If the conflict or the collision can be removed in this manner, i.e. by modifying the straight segment length, than the new or actual sliding way is recorded. On the other hand, if the conflict persists, then the optimization step has failed, and the conflict is recorded at the neighbor.

Next, at step 616, a determination is made for collision in the neighbor bracket slot:

(a) No collision: If a collision is not detected without the need for optimization to modify the straight segment, then the original actual sliding way is marked acceptable and recorded without change. On the other hand, if a potential collision was removed through optimization, then the new (modified) sliding way is recorded, and the possible sliding movements of the arch wire in the tangential and antitangential directions are corrected.

(b) Collision: If a collision is detected which could not be corrected through optimization, then the depth of the insertion of the arch wire in the neighbor bracket slot as well as the original sliding way are recorded.

Figure 19:
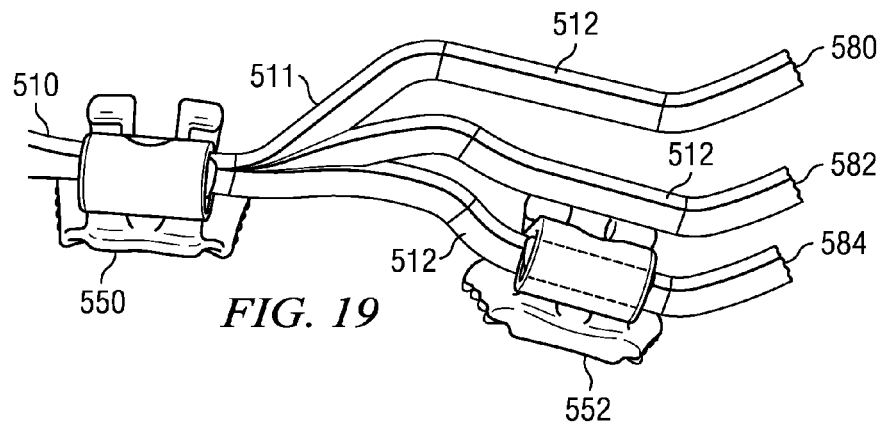
FIG. 19 illustrates the virtual arch wire insertion in a virtual neighbour bracket slot without collision, according to a preferred embodiment of the invention. The results of incremental iteration steps to simulate the deformation of the virtual arch wire are shown.

FIG. 19 presents an enlarged view of a portion of the illustration between the virtual bracket 550 and the virtual bracket 552 in FIG. 17; and the straight segments 510 and 512, and the bent segment 511 of the arch wire in FIG. 16. FIG. 19 illustrates insertion of the straight segment 512 into the slot of the virtual bracket 552 in incremental steps 580, 582 and 584. As can be seen from FIG. 17, the straight segment 512 is inserted into the slot of the virtual bracket 552 without conflict or collision. The results of incremental iteration steps to simulate the deformation of the virtual arch wire are shown. Due to the successively corrected forces and moments applied during the simulated insertion process, the virtual arch wire end approaches the virtual neighbour bracket slot the placement of which corresponds to the malocclusion state of the patient. Virtual teeth are hidden from view in FIG. 19.

Next, at step 618, the neighbor is designated as the selected bracket slot and movements in the tangential and antitangential directions are computed. The process then moves back to step 612.

Figure 20:
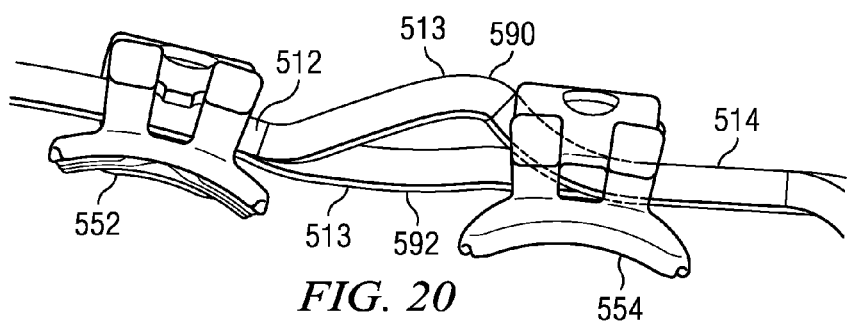
FIG. 20 illustrates the virtual arch wire insertion in a virtual neighbour bracket slot with collision, according to a preferred embodiment of the invention.

FIG. 20 presents an enlarged view of a portion of the illustration between the virtual bracket 552 and the virtual bracket 554 in FIG. 17; and the straight segments 512 and 514, and the bent segment 513 of the arch wire in FIG. 16. FIG. 19 illustrates insertion of the straight segment 514 into the slot of the virtual bracket 554 in incremental steps 590 and 592. As can be seen from FIG. 17, the straight segment 514 is inserted into the slot of the virtual bracket 554, which is shown transparent for the illustration purposes, with a conflict or collision as a portion of the bent segment 513 gets inserted into the slot as well. Optimization to remove the conflict or collision was unsuccessful in this case, so the conflict or collision was recorded for the virtual bracket 554. Here again, the virtual teeth are hidden from the display in FIG. 20.

At step 620, a check is made to determine if the selected direction for evaluation is antitangential. If the answer at step 620 is in the negative, the process moves to step 622; otherwise to step 624.

At step 622, the starting point bracket slot is reset as the selected bracket slot; and the antitangential direction is selected for the arch wire insertion evaluation. The process then moves back to step 612.

In this manner, the simulation process is repeated until the target virtual arch wire insertion is evaluated for the entire virtual arch wire with respect to all the virtual brackets which are placed corresponding to the malocclusion state of the patient.

At step 624, the results of the arch wire insertion simulation are evaluated as follows:

(a) In case of no collisions or conflicts, including the collisions or conflicts which could be removed with modified straight segments, the sum of the necessary actual sliding ways in all of the virtual bracket slots is computed; and the starting point and the placement of the arch wire are recorded as acceptable for the arch wire insertion.

(b) In case of non-resolvable collisions, the starting point is recorded as unacceptable for the arch wire insertion; and the sum of the virtual arch wire insertion depths into each virtual bracket slot as well as the sum of the necessary sliding ways are computed and recorded for potential use in redesigning the arch wire.

Figure 21:
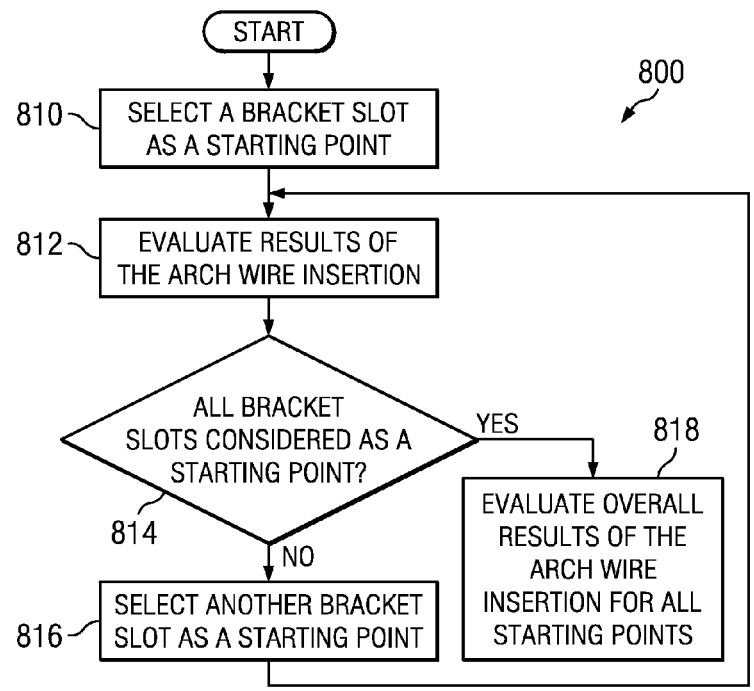
FIG. 21 shows a flow chart for selecting the best starting point for inserting the virtual arch wire into the brackets, according to another preferred embodiment of the invention.

Next, FIG. 21 shows a flow chart 800 for selecting the best starting point for inserting the virtual arch wire according to another preferred embodiment of the invention. In order to select the best starting point, basically, each virtual bracket is selected as a potential starting point for evaluating the quality of the virtual arch wire insertion, and the process of FIG. 18 is repeated.

At step 810, a virtual bracket slot is selected as a starting point.

Next, at step 812 the results of the virtual arch wire insertion are evaluated for the starting point bracket slot. The entire evaluation process described in the flow chart of FIG. 18 is used at step 812.

Next, at step 814, a determination is made whether all bracket slots have been considered as a starting point or not? If the answer is in the negative, the process moves to step 816; otherwise to step 818.

At step 816, another virtual bracket slot is selected as a starting point; and the process is repeated from step 812.

At step 818, overall results of the arch wire insertion for all starting points are evaluated. From the evaluation, the best starting point for the arch wire insertion is determined as follows:

(a) Only one starting point without collisions or conflicts: this bracket slot is recommended as starting point.

(b) Several starting points without collisions or conflicts: the bracket slot requiring the minimum sum of the arch wire actual sliding ways is recommended for start.

(c) No starting point without collisions: the arch wire redesign from the treatment planning perspective is recommended. However, the user is informed of the bracket slot with the minimum arch wire insertion depth into the brackets, and a warning is shown; and the use of the arch wire is left to the user.

In summary then, the invention disclosed herein offers three potential outcomes for the arch wire custom designed during the treatment planning regarding the wire's capability for insertion into the brackets placed on the dentition of a patient in malocclusion state through the simulation exercise of the virtual arch wire insertion evaluation: (a) the arch wire is capable of insertion without conflicts or collisions, (b) the arch wire as designed poses conflicts which van be overcome through the automatic optimization of the straight segments of the arch wire by the software, and (c) the arch wire as designed poses conflicts which cannot be overcome through the automatic optimization of the straight segments of the arch wire. Additionally, the invention disclosed herein enables the user in automatically selecting the best insertion starting point as to the bracket in the event that there are no conflicts either to begin with or through the redesign of the arch wire through optimization.

In another embodiment of the invention, the forces and moments at the virtual brackets are estimated by the arch wire insertion evaluation software routine, and the user is informed about the applied forces and moments indicating critical areas, e.g., violation of biological constrains or treatment objectives, during the treatment planning and arch wire design process.

Additionally, the invention lets the user evaluate other options for the arch wire design. For example, the user has the option to manipulate the wire outline by manually changing the sliding ways to remove collisions, which are not solved automatically. If this is not possible, the treatment can be planned in stages; and the arch wire can be designed and evaluated for the insertion quality accordingly. For example, the practitioner may prefer using limit arch wires (e.g. 50% of target). As another option, the practitioner may evaluate the scenario of partial ligature tied in to the bracket for a defined period of time. The practitioner may evaluate yet another option of repositioning the brackets or re-bonding the brackets in the case where the brackets are already placed on the teeth of the patient. The treatment planning software in combination with the novel arch wire insertion evaluation software described herein enables the user or the practitioner in evaluating the variety of options described above; and there by selecting the option best suited to the patient. One skilled in the art would appreciate that the over all treatment options, including the arch wire design and implementation, discussed above are for example purposes only, and not meant to present an exhaustive list for application of the instant invention.

Because the hand-held scanner allows for scans of the dentition in a matter of minutes, the scanner becomes an important tool in monitoring treatment. As the treatment progresses, the movement and position of the teeth during treatment can be quantified with a high degree of precision by taking scans of the patient's dentition with brackets mounted on the teeth of the patient. The orthodontist can discern during treatment that corrections in the wire need to be made, for example due to biological influences affecting tooth movement. The treatment planning software on the workstation displays the current situation, and also the target situation. A new customized arch wire is designed and evaluated for insertion quality on the computer. The relevant information for making the new arch wire is sent to the precision appliance service center and a new arch wire is manufactured and shipped to the clinic.

Finally, The complete design of the arch wire is provided in a CNC data file for the arch wire-bending robot located at the precision appliance center 26 of FIG. 1. The robot manufactures the custom arch wire in accordance with the final design. The robot has six degrees of freedom in movement, so complex, non-planar bends in the arch wire can be realized. Additionally, a transfer tray is manufactured to assist the orthodontist in placing the brackets at the proper location on the dentition of the patient. The transfer tray, brackets and arch wire are shipped to the orthodontist's clinic 22. The orthodontic appliance is then applied to the patient and treatment commences. For further details on arch wire design and manufacturing, refer to the patent application of Butscher et al., filed Apr. 13, 2001, entitled ROBOT AND METHOD FOR BENDING ORTHODONTIC ARCHWIRES AND OTHER MEDICAL DEVICES, Ser. No. 09/834,967, now issued as U.S. Pat. No. 6,612,143, the entire contents of which are incorporated by reference herein.

Presently preferred and alternative embodiments of the invention have been set forth. Variation from the preferred and alternative embodiments may be made without departure from the scope and spirit of this invention.

We claim:

1. A method of determining one or more recommended starting points for inserting a virtual target custom arch wire into a set of virtual brackets, comprising the steps of:
    (a) obtaining a model of a set of virtual of brackets placed up on the virtual teeth of a patient in a jaw in an initial state;
    (b) obtaining a virtual model of a target custom arch wire designed to be inserted into said virtual brackets; wherein said custom arch wire comprises alternating sequence of straight segments and bent segments; wherein each of said straight segments is designated to be inserted into the slot of a specific virtual bracket from said set of virtual brackets;
    (c) selecting a virtual bracket from said set of virtual brackets as a starting point;
    (d) inserting the designated straight segment of said target custom arch wire into the slot of said starting point virtual bracket;
    (d) inserting said target custom arch wire successively into the slot of each of said virtual brackets remaining from said set of virtual brackets first on one side of said starting point virtual bracket and then the other side; wherein if at least one bent segment or a portion thereof is unavoidably inserted into a bracket slot, then the arch wire insertion is identified as having collision; and otherwise collision-free;
    (e) finding the total length of said straight segments;
    (f) repeating steps (c)-(f) until each of the virtual brackets from said set of virtual brackets has been considered as a starting point virtual bracket; and
    (g) selecting one or more of said starting point virtual brackets having collision-free arch wire insertion and minimal total length of straight segments as recommended starting points for arch wire insertion; wherein step (d) further comprises optimizing said target arch wire if a collision is detected during step (d); wherein said step of optimizing said target custom arch wire comprises modifying the length of the straight segment so as attempt to remove said collision.

2. The method of claim 1, wherein said jaw is the upper jaw of said patient.

3. The method of claim 1, wherein said jaw is the lower jaw of said patient.

4. The method of claim 1, wherein the geometry of said target custom arch wire is non-planar in three-dimensions.

5. The method of claim 1, wherein said initial state comprises the patient's dentition in malocclusion.

6. The method of claim 1, wherein said initial state comprises the patient's dentition in an intermediate state during the course of the treatment.

7. The method of claim 1, further comprising step (h) of displaying said target custom arch wire and said virtual brackets to a user.

* * * * *